(12) United States Patent
Bruder et al.

(10) Patent No.: US 6,556,697 B1
(45) Date of Patent: Apr. 29, 2003

(54) IMAGE RECONSTRUCTION METHOD

(75) Inventors: Herbert Bruder, Hoechstadt (DE); Thomas Flohr, Uehlfeld (DE); Bernd Ohnesorge, Erlangen (DE); Stefan Schaller, Fuerth (DE); Bernhard Scholz, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/396,337

(22) Filed: Sep. 15, 1999

(30) Foreign Application Priority Data

Sep. 15, 1998 (DE) .......................................... 198 42 238
Sep. 15, 1998 (DE) .......................................... 198 42 240

(51) Int. Cl.[7] .................................................. G06K 9/00
(52) U.S. Cl. ........................... 382/131; 382/132; 378/8; 378/95
(58) Field of Search ................................. 382/128, 131, 382/132; 378/8, 95

(56) References Cited

U.S. PATENT DOCUMENTS

| | | | | |
|---|---|---|---|---|
| 4,149,079 A | * | 4/1979 | Ben-Zeev et al. | 378/14 |
| 4,868,747 A | * | 9/1989 | Mori et al. | 378/901 |
| 5,170,439 A | * | 12/1992 | Zeng et al. | 378/901 |
| 5,265,013 A | * | 11/1993 | King et al. | 128/922 |
| 5,751,782 A | * | 5/1998 | Yoshitome | 378/98.5 |
| 5,832,051 A | * | 11/1998 | Lutz | 378/8 |
| 5,848,114 A | * | 12/1998 | Kawai et al. | 378/4 |
| 5,889,525 A | * | 3/1999 | De Murcia et al. | 345/420 |
| 6,002,738 A | * | 12/1999 | Cabral et al. | 378/15 |
| 6,047,080 A | * | 4/2000 | Chen et al. | 382/128 |
| 6,149,592 A | * | 11/2000 | Yanof et al. | 600/427 |
| 6,154,516 A | * | 11/2000 | Heuscher et al. | 378/15 |
| 6,236,705 B1 | * | 5/2001 | Stergiopoulos et al. | 378/8 |

FOREIGN PATENT DOCUMENTS

| | | |
|---|---|---|
| EP | 0 370 341 | 5/2000 |
| WO | WO 99/07283 | 2/1999 |

* cited by examiner

Primary Examiner—Samir Ahmed
Assistant Examiner—Anaud Bhatnagar
(74) Attorney, Agent, or Firm—Schiff Hardin & Waite

(57) ABSTRACT

In an image reconstruction method for imaging a periodically moving object with a computed tomography apparatus employing a multi-line detector unit, suitable selection of the rotational speed of the carrier of the computed tomography apparatus and employment of a three-dimensional back-projection algorithm, allow qualitatively high-great images of the object to be produced in every motion phase.

26 Claims, 5 Drawing Sheets

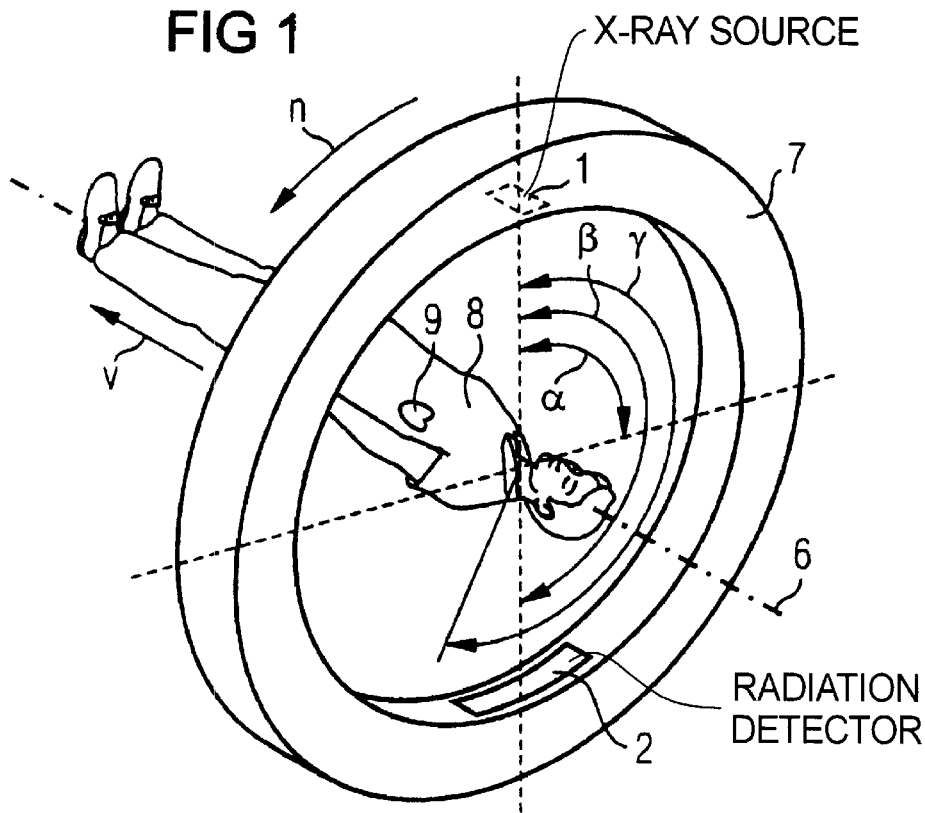
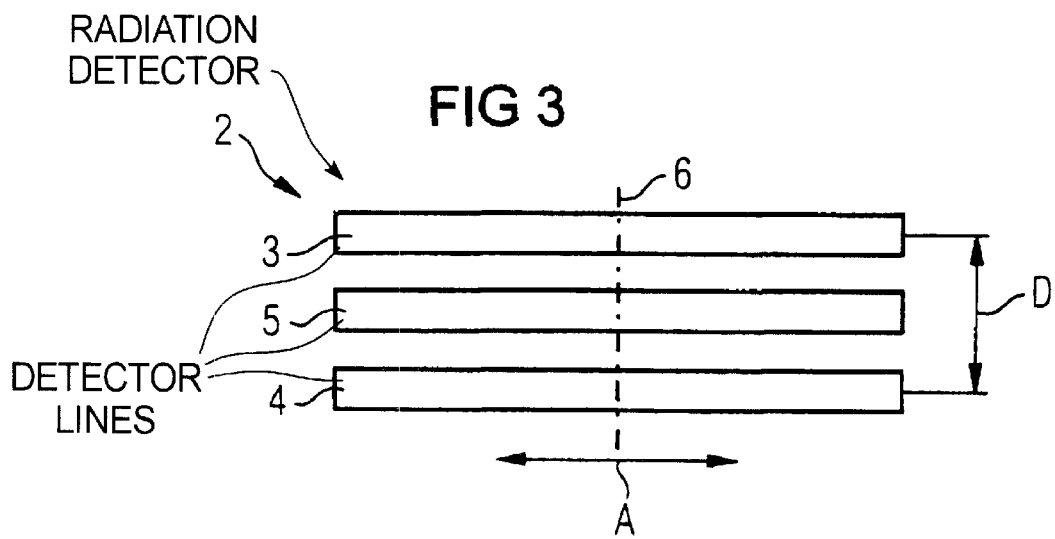

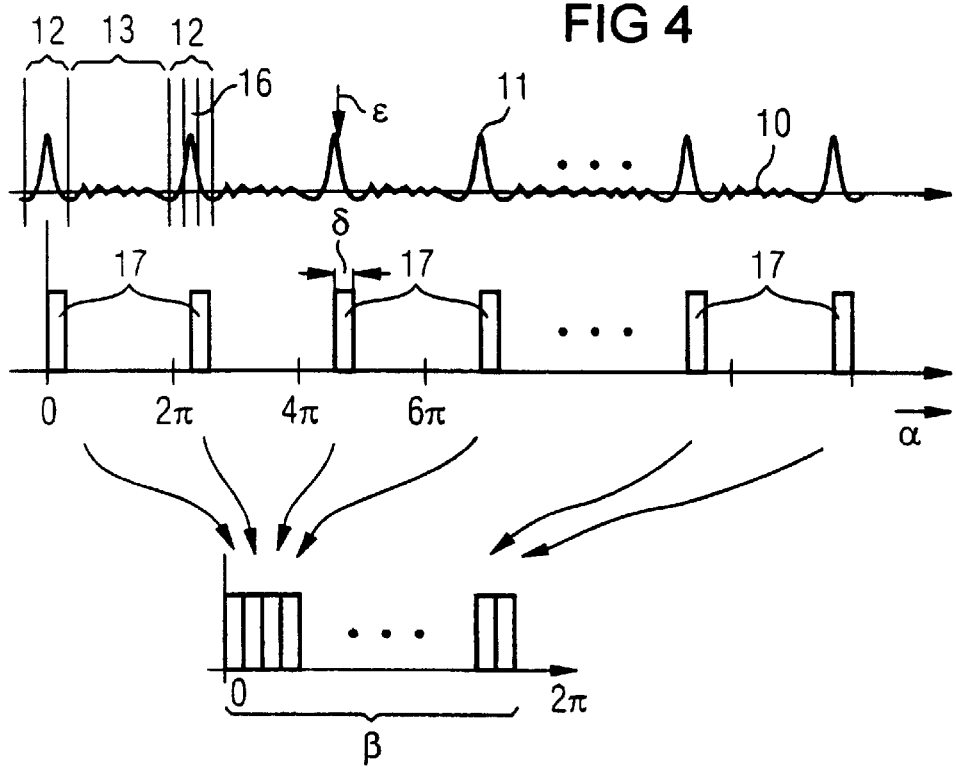
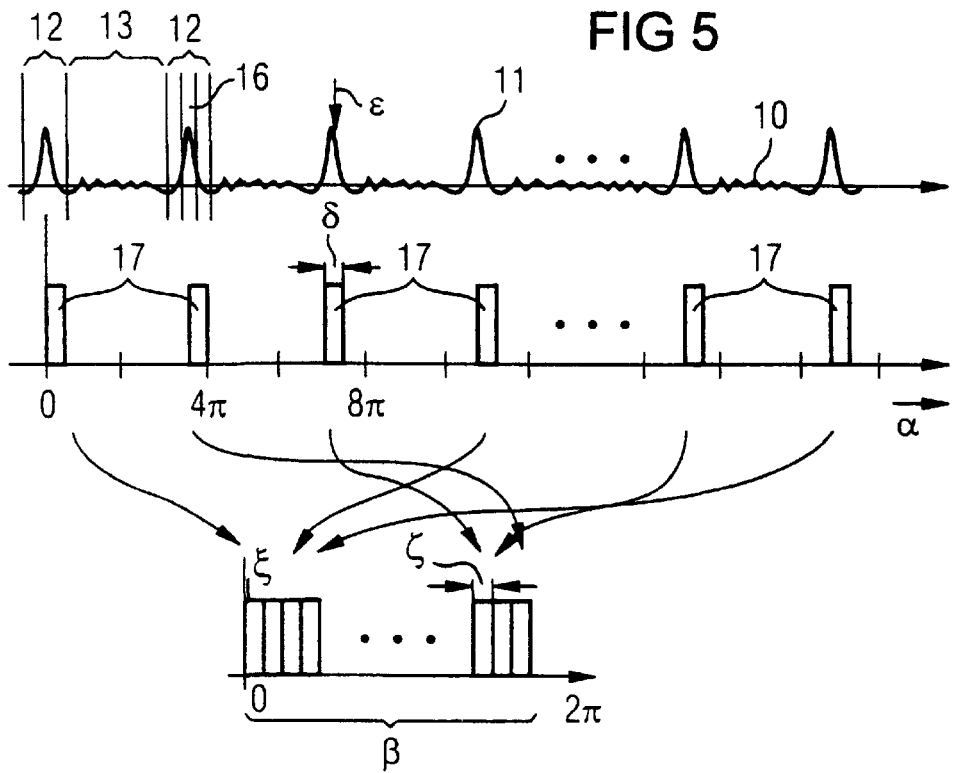

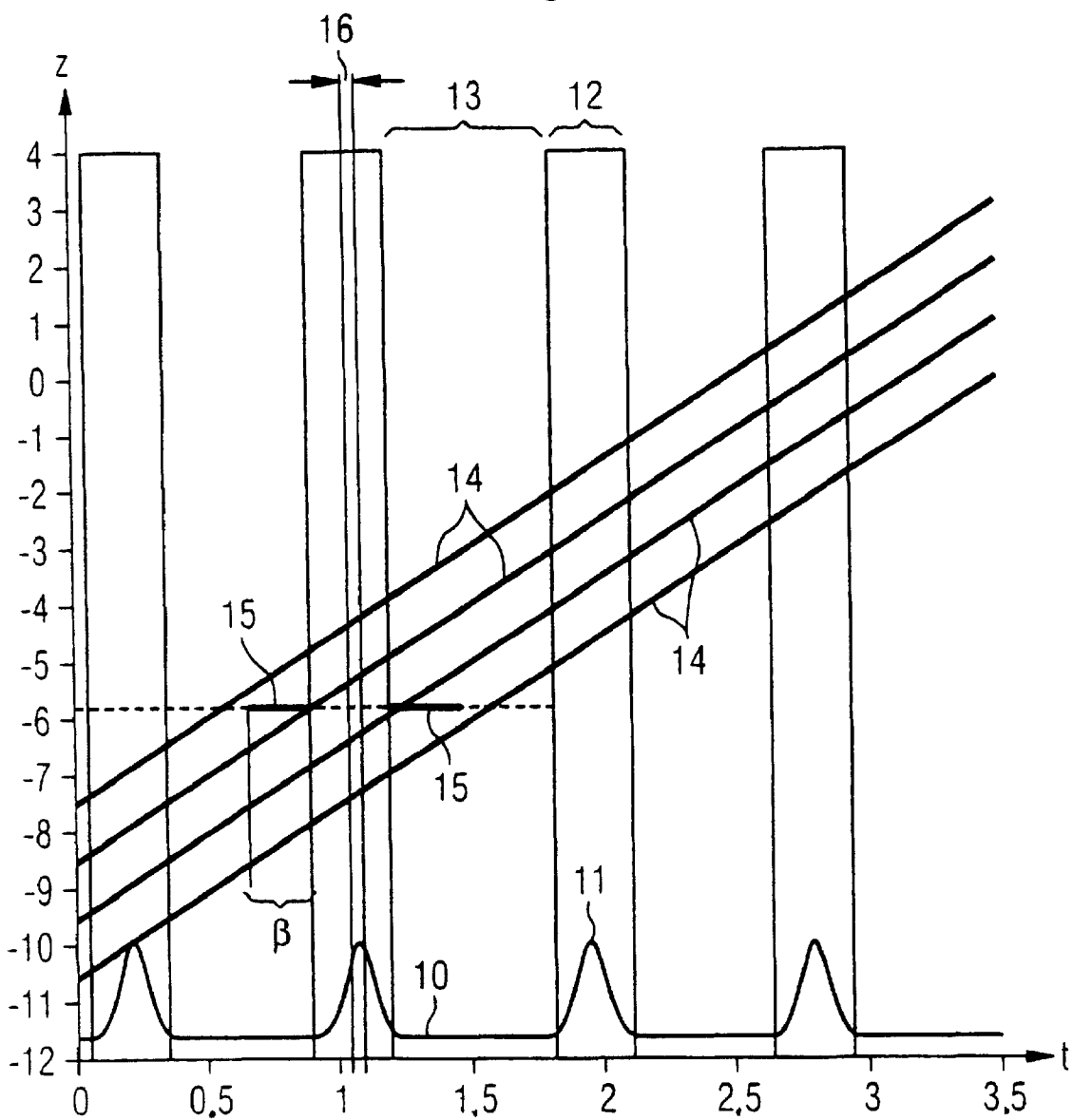

IMAGE RECONSTRUCTION METHOD

BACKGROUND OF THE INVENTION

1. Field of the Invention

The present invention is directed to a method for reconstructing an image of a periodically moving object of the type employing a detector unit arranged on a carrier, the carrier rotating around a rotational axis with a rotational speed.

2. Description of the Prior Art

Measured datasets of a heart are conventionally registered with a detector unit having a single detector line that is arranged at a right angle relative to the rotational axis. During rotation of the carrier, measured datasets are registered by the detector line at a number of rotational angles. At the same time, a ECG signal is registered. Rotational angles are allocated to heart phases by means of the ECG signal. The heart exhibits a moving phase and an idle phase in each period. Image reconstructions are undertaken using registered measured datasets representing the idle phases. Subsequently, the patient is shifted a small distance parallel to the rotational axis and new measured datasets are registered.

Given standard rotational speeds (maximum of 120 revolutions/minute), it is not possible to tomographically image the complete human heart during the time span for which a patient can hold his or her breath, i.e. during a breath-holding pause.

It is also known to continuously shift the patient during the rotation of the carrier (what is referred to as a spiral scan) and to likewise continuously register measured datasets (referred to as spiral data), however, limits are quickly encountered. Not all shift or slice positions can be reconstructed from measured data registered during the idle phase of the heart. In the interpolation of the spiral data based on a predetermined shift or slice position, it is therefore necessary to interpolate using only data obtained during spiral revolutions that took place in the resting (idle) phase of the heart. This can substantially increase the interpolation width (i.e., the spacing between measured datasets which are used to produce an interpolated dataset therebetween) and consequently significantly reduce the image sharpness that can be achieved.

It is fundamentally possible to reconstruct an image of the object at all shift positions, however, only images which are qualitatively poor can be achieved at the shift position during which the heart was in a beating (moving) phase.

SUMMARY OF THE INVENTION

An object of the present invention is to provide an image reconstruction method with which qualitatively high-grade images of periodically moving objects can be registered and reconstructed with high time resolution, even with a conventional computed tomography apparatus.

For a subject exhibiting periodic motion with a motion phase and a resting phase, the object is achieved in a method wherein data are obtained from a detector unit having a first detector line and a last detector line, the detector lines proceeding substantially at a right angle relative to the rotational axis, wherein the presence of resting phases is identified and respective measured datasets respectively allocated to the rotational angles are registered at least during the resting phases at a number of rotational angles per rotational angle by each of the detector lines simultaneously, wherein the duration of the resting phase is identified and the rotational speed is selected such that the carrier rotates during a resting phase by a rotational angle that is at least as large as the reconstruction angle range required for the reconstruction of the image of the object, and wherein an image of the object is reconstructed from the measured datasets with a three-dimensional back-projection algorithm.

In this embodiment, measured datasets can be registered during the resting phases in such a large, continuous rotational angle range that a reconstruction of the object is possible, and the use of the three-dimensional back-projection algorithm substantially enhances the quality of the reconstructed image. The use of a multi-line detector unit considerably shortens the registration time. By combining the measures of a multi-line detector unit, registration of the measured datasets in the resting phases, suitable selection of the rotational speed, and use of a three-dimensional back-projection algorithm, qualitatively high-grade images of the object thus can be registered and reconstructed.

This image reconstruction method embodiment is preferably utilized for imaging the human heart. For determining the presence of a resting phase and the duration of the resting phase of the human heart, an electrocardiogram of the human is thereby preferably monitored.

When the periodic motion of the subject, by contrast, exhibits no resting phase or only a short resting phase or registrations of the subject should ensue during the motion phase, the object of the invention is achieved in a method wherein data are obtained from a detector unit having a first detector line and a last detector line, the detector lines proceeding substantially at a right angle relative to the rotational axis, wherein a measured dataset allocated to respective rotational angles are registered during a number of periods at a number of rotational angles, simultaneously by each the detector line per rotational angle, wherein the presence of phase ranges are identified with respective phase reference points of the periodic motion of the object, and the measured datasets are registered at least during such phase ranges, wherein the duration of the phase ranges is identified and the product of the number of periods and a phase angle range swept during the phase range corresponds to at least a reconstruction angle range required for the reconstruction of an image of the object, and wherein an image of the object is reconstructed from the image datasets with a three-dimensional back-projection algorithm.

This image reconstruction method embodiment is preferably utilized for imaging the human heart and the phase range lies in the beat phase of the human heart. For determining the phase range, an electrocardiogram of the human heart is again preferably monitored.

The x-ray source can be triggered with the electrocardiogram, so that the object is only transirradiated during the phase ranges, the examined patient is subjected to an especially low x-ray dose.

The rotational speed of the carrier can be selected such that the measured datasets of immediately succeeding rotational angles are registered during the phase range of the same period, or during the phase range of the immediately following periods, so that the image reconstruction is especially simple. When, by contrast, the rotational speed of the carrier is selected as high as possible, the examined patient is subjected to a lower x-ray dose.

construction of an overall measured dataset adequately large for the image reconstruction can, for example, ensue by combining, per phase angle, the measured datasets registered during the phase range are combined per phase range to form a respective rotational angle group, identifying a reference angle corresponding with the phase reference point for each rotational angle group, identifying, per rotational angle, the rotational angle groups whose reference angle is maximally as large as that of the respective rotational angle, and utilizing the measured datasets of that rotational angle group within the rotational angle groups identified in this way for reconstruction of an image of the object, at which the difference between the respective rotational angle and the respective reference angle is minimal.

Alternatively, the overall measured dataset can be constructed by dividing the reconstruction angular range into a number of sub-angle ranges of identical size, each having a respective sub-angle range reference angle, combining, per phase range, the measured datasets registered during the phase range, to form a respective rotational angle group, identifying, for each rotational angle group, a reference angle corresponding to the phase reference point, and utilizing, per sub-angle range, the measured datasets of that rotational angle group at which the absolute value of the difference between the respective sub-angle range reference angle and the respective reference angle is minimum for the reconstruction of an image of the object.

Given a change from one rotational angle group to another rotational angle group, the measured datasets can be weighted and superimposed in an overlap region, so that a higher image quality can be achieved.

When the examination ensues in the form of a spiral scan, the inventive method including obtaining a data from a detector unit having a first detector line and a last detector line, the detector lines proceeding substantially at a right angle to a rotational axis and parallel to the rotational axis and being spaced from one another by a detector width, shifting the object along the rotational axis relative to the carrier with a feed rate and rotating the carrier around the rotational axis with a rotational speed, identifying, per rotational angle, the presence of resting phases and, for each of a number of rotational angles, registering respective measured datasets allocated to the respective rotational angle simultaneously with the detector rows during the resting phases, identifying the duration of the resting phases and selecting the rotational speed such that the carrier rotates during a resting phase through a rotational angle that is at least as large as the reconstruction angular range required for the reconstruction of the object, and selecting the feed rate such that the object is maximally shifted along the rotational axis by the detector height during the sum of a motion phase and two reconstruction times, with the reconstruction time being the time required for sweeping the reconstruction angular range.

In this embodiment, namely, measured datasets can be registered during the resting phases in such a large continuous rotational angle range that, using a known interpolation between the connector lines for each slice or shift position registered within this resting phase, a reconstruction of the object is possible with back-projection algorithms that are well-known in computed tomography. A feed of the object that is not too fast ensues in the motion phases, so that the shift positions registered in the following resting phase merge seamlessly with the previously register shift positions. By combining the measures of a multi-line detector unit, registration of the measured datasets in the resting phases, and suitable selection of feed rate and rotational speed, qualitatively high-grade images of the object thus can be registered and reconstructed with known reconstruction algorithms.

When, by contrast, the periodic motion of the object exhibits no resting phase or only a short resting phase or registrations of the object are to ensue during the motion phase, alternatively for spiral scans the method includes obtaining data from a detector unit having first detector line and a last detector line, the first and the last detector lines proceeding at a right angle relative to the rotational axis and being spaced from one another by a detector width parallel to the rotational axis, shifting the object along the rotational axis relative to the carrier with a feed rate, and rotating the carrier rotates around the rotational axis with a rotational speed, for each a number of rotational angles registering respective measured datasets allocated to the respective rotational angle simultaneously with the detector lines, identifying the presence of phase ranges with respective phase reference points of the periodic motion of the object, and registering the measured datasets at least during such phase ranges, selecting the feed rate such that the object exhibits a number of periods during the feed within the detector width, and identifying the duration of the phase ranges, with the product of the number of periods and a phase angle range swept during the phase range at least corresponding to a reconstruction angular range required for reconstruction of the object.

This measured data registration method embodiment is preferably utilized for imaging the human heart and when the phase range lies in the beating phase of the human heart.

An electrocardiogram of the human heart is again preferably monitored for the determination of the phase range.

DESCRIPTION OF THE DRAWINGS

FIG. 1 is a perspective view of a computed tomography apparatus for implementing the inventive method.

FIG. 3 is a schematic illustration of the detector unit of the computed tomography apparatus according to FIGS. 1 and 2.

FIG. 4 schematically illustrates a sorting technique used in the inventive method.

FIG. 5 schematically illustrates a further sorting technique used in the inventive method.

FIG. 7 schematically illustrates the registration of measured datasets in accordance with the inventive method.

DESCRIPTION OF THE PREFERRED EMBODIMENTS

Figure 2:
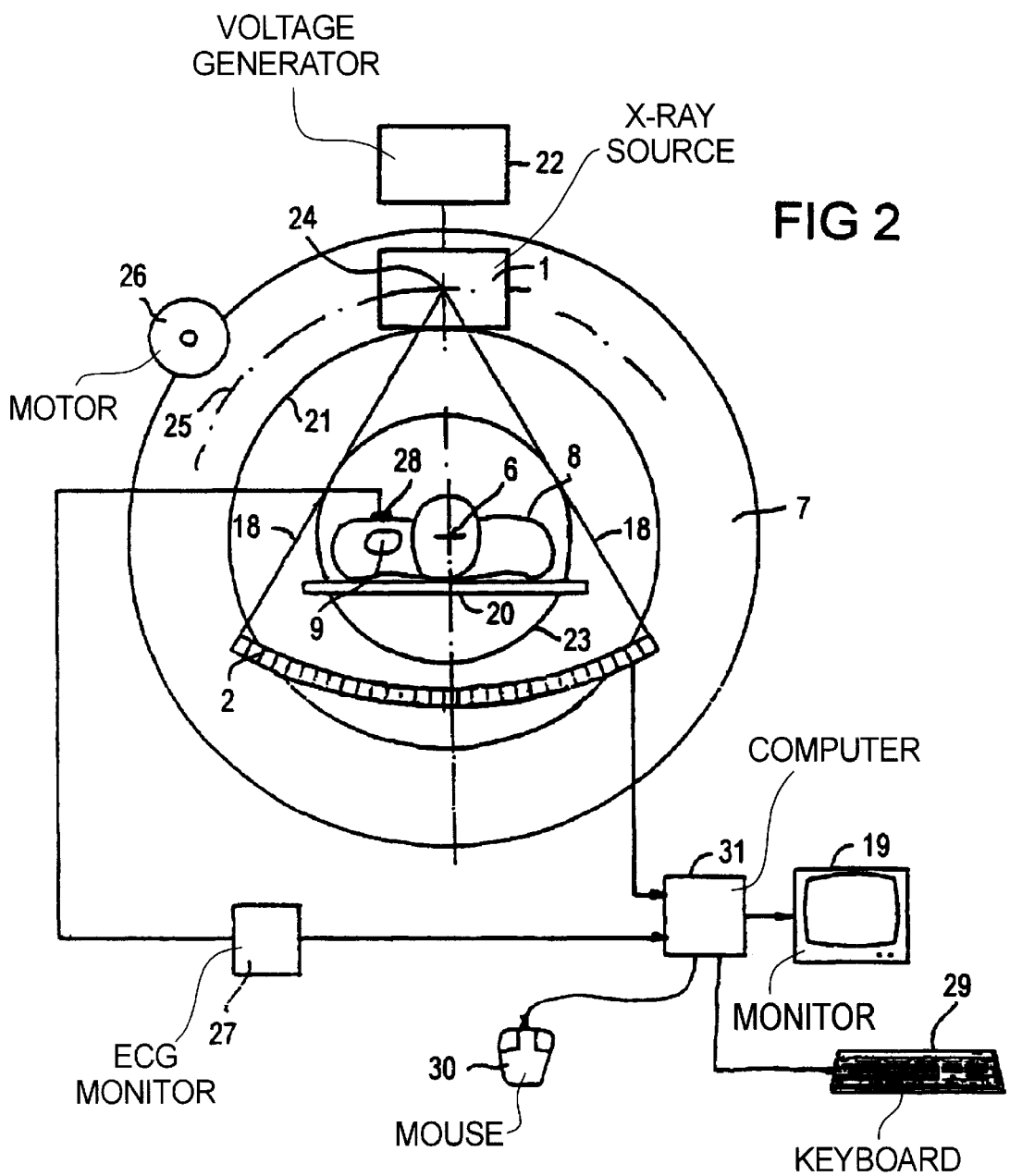
FIG. 2 is an end view of the computed tomography apparatus according to FIG. 1, with electronic components shown in block diagram form.

FIGS. 1 and 2 schematically show a computer tomograph for implementation of the inventive method.

The computed tomography apparatus has a measuring unit composed of an x-ray source 1 that emits an x-ray beam 18 and a radiation detector unit 2 that is composed of a number of lines of individual detectors. Each line contains, for example 512 individually detectors, following one another in the direction of a rotational axis 6. The focus of the x-ray source 1 from which the x-ray beam 18 emanates is referenced 24. The examination subject, a human patient 8 in the case of the illustrated exemplary embodiment, lies on a table 20 that extends through the measuring opening 21 of an annular carrier 7, referred to as the gantry.

The detector unit 2 according to FIG. 3 has a first detector line 3 and a last detector line 4. As shown, one or more further detector lines 5 can be arranged between the first and the last detector lines 3 and 4.

The detector lines 3 through 5 proceed at a right angle to the rotational axis 6 as indicated by the arrow A. Parallel to the rotational axis 6, the first detector line 3 and the last detector line 4 are spaced from one another by a detector width D. The detector width D is thereby measured from line center to line center. The x-ray source 1 is supplied by a voltage generator 22. The x-ray source 1 and the detector unit 2 are mounted opposite one another at the carrier 7 such that the x-ray beam 18 emanating from the x-ray source 1 strikes the detector unit 2. The carrier 7 is mounted so as to be rotatable around the rotational axis 6 of the computed tomography apparatus, which represents the system axis, with a rotational speed n for scanning the patient 8. The x-ray beam 18 emanating from the x-ray source 1 covers a measuring field 23 having a circular cross-section. The focus 24 of the x-ray source 1 moves on a focus path 25 curved circularly around a rotational center lying on the rotational axis 6.

The x-ray beam 18 transirradiates the patient 8, and the x-rays striking at detector unit 2 are detected at a number of rotational angles α during the rotation and are combined to form a measured dataset for that angle α. A measured dataset is thus the totality of measured data simultaneously registered by the detector lines 3 through 5 at a rotational angle α and allocated to this rotational angle α.

From the totality of registered measured datasets, which proceed from the detector unit 2 to a computer 31, which reconstructs an image of an object to be examined and displays this image on a monitor 19.

The drive 26 allocated to the carrier 7, is suited for allowing the carrier 7 to rotate continuously. Further, another drive (not shown in the figures) is provided that enables a relative displacement between the table 20 and thus the patient 8, and the carrier 7 together with the measuring unit 1, 2 in the direction of the rotational axis 6. There is thus the possibility of scanning three-dimensional regions of the patient 8.

This can occur in the form referred to as a sequence scan, wherein a region of the patient 8, whose extent in the direction of the rotational axis 6 corresponds to the detector height D, is respectively scanned, and subsequently the table 20 is shifted in the direction of the rotational axis 6 by a distance (increment) corresponding to the detector height D, whereupon the patient 8 is re-scanned. This procedure can be repeated until the respective region of interest of the patient 8 has been completely scanned.

There also is the possibility of implementing a spiral scan, wherein a three-dimensional region of the patient 8 is scanned, by continuously rotating the carrier 7 together with the measuring unit 1, 2 with the relative displacement of bearing table 20 and carrier 7 in the direction of the rotational axis 6 ensuing at the same time with a feed rate v.

For the implementation of examinations of the heart or of heart-proximate regions of the body of the patient 8 moving in rhythm with the heart action, the computed tomography apparatus according to FIGS. 1 and 2 also has a known electrocardiogram monitor 27 that can be connected to the patient 8 via electrodes, one thereof being shown in FIG. 2 and being referenced 28, serving the purpose of acquiring the electrocardiogram (ECG) of the patient 8 in parallel with the examination with the computed tomography apparatus. Preferably digital data corresponding to the ECG signal are supplied to the computer 31, that interprets the data and displays the data as needed as an ECG trace on the monitor 19.

The electrodes of the electrocardiogram monitor 27 are attached to the body of the patient so that insofar as possible that they do not negatively influence the examination of the patient 8.

A keyboard 29 and a mouse 30 that enable operation of the computed tomography apparatus are connected to the computer 31.

In order to be able to reconstruct meaningful images of the examined object, measured datasets for successive rotational angles α are required, these extending over a reconstruction angular range β. The reconstruction angular range β lies on the order of magnitude of at least 180°.

Insofar as an image of body parts of the patient 8 that can be placed at rest are to be tomographically registered, no noteworthy problems arise for the registration of the measured datasets. Problems arise, by contrast, in the registration of measured datasets of a periodically moving object. One example of such an object is the human heart 9, which is schematically shown in FIG. 1.

As is known, the human heart 9 performs an essentially periodic motion. The periodic motion is thereby composed of an alternating sequence of a resting or relaxation phase and a motion or beating phase. The relaxation phase has a duration between, usually, 500 and 800 ms; the beating phase has a duration of 200 through 250 ms.

The rotational speed n of the carrier 7 usually lies at 45 through 120 revolutions per minute. By comparing the rotational speed n to the duration of the relaxation phase of the heart 9, one can easily determine that the carrier 7 rotates through a rotational angle γ in the relaxation phase of the heart 9 that lies between 135° (500 ms given 45 revolutions per minute) and 576° (800 ms given 120 revolutions per minute).

When the rotational speed n is selected high enough, the carrier 7 rotates through a rotational angle γ during the resting phase that is greater then the reconstruction angular range β required for the reconstruction of the object 9. It is thus possible to register complete measured datasets during the resting phases of the heart 9, so that the image of the heart 9 can be reconstructed in the register region.

Given implementation of a sequence scan, the patient 8 is respectively displaced parallel to the rotational axis 6 by a feed increment after the registration of the required measured datasets. The feed increment is maximally as large as the detector width D. In the next resting phase of the heart 9, new measured datasets are then registered. This executive sequence is repeated until the entire heart 9 of the patient 8 has been tomographically registered.

An image of the heart 9 is reconstructed from the totality of registered measured datasets. Due to the utilization of a multi-line detector unit 2, some of the x-rays, however, have penetrated the heart 9 at an angle relative to the rotational plane of the carrier 7. A reconstruction of an image of the heart 9 with the two-dimensional back-projection algorithms which are known in computed tomography thus leads to systematic errors. In order to avoid these errors, the image of the heart 9 is therefore reconstructed from the measured datasets with a three-dimensional back-projection algorithm. Such a back-projection algorithm has been published, for example, by L. A. Feldkamp, L. C. Davis and J. W. Kress in the Journal of the Optical Society of America A, Volume 1, No. 6, pages 612 through 619 (JOSAA, January 1984, No. 6, pp. 612–619).

As already mentioned, the electrocardiogram 10 of the human heart 9 is monitored in order to be able to identify the resting phases 13 of the human heart 9 therefrom. As warranted, the electrocardiogram 10 can also be used in order to correspondingly trigger the x-ray source 1, for example an x-ray tube, so that it only emits x-rays during the resting phases 19 of the heart 9. In this way, the radiation load on the patient 8 can be reduced. Moreover, the carrier 8 in this measured data registration method should rotate with the highest possible rotational speed n.

The above-described method embodiment cannot be employed when the human heart 9 is to be registered during a phase range 16 that lies in the beating phase 12, since the phase range 16 has a time duration that is substantially shorter then the reconstruction time T. The phase range 16 can, for example, have a duration of 50 ms. During this time, the carrier 7 only rotates by 36° given a rotational speed n of 120 revolutions per minute, one-fifth of the minimum reconstruction angular range $\beta$. Nonetheless, the heart 9 also can be imaged in this phase range 19 with the same computed tomography apparatus. This occurs as follows.

As previously, measured datasets allocated to the respective rotational angle $\alpha$ are simultaneously registered by the detector lines 3 through 5 at a number of rotational angles $\alpha$. The measured datasets are registered at least during the phase range 16 of the periodic motion of the heart 9. The heart 9 experiences a number of periods. The number of periods is derived from the condition that the product of the number of periods and a phase angle range $\delta$ must at least correspond to the reconstruction angle range $\beta$. The phase angle range $\delta$ is thereby the angle swept by the carrier 7 during the duration of the phase range 16. As a safety margin, the number of periods should be 1½ through 2 times as large as the minimum plurality of periods. The carrier 7, for example, executes a number of rotations that typically lies between 10 and 20. During these rotations, the human heart 9 beats approximately 5 through 20 times. It thus experiences 5 through 20 periods.

It is assumed as an example in FIG. 4 that the phase range 16 has a duration of 50 ms and that the carrier 7 rotates with a rotational speed n of 120 revolutions per minute. Given these assumptions, the carrier 7 sweeps a phase angle range $\delta=36°$ during a phase range 16. Given the further assumption that the reconstruction angle range $\beta$ amounts to 180°, at least 5 and preferably through 10 beating phases 12 of the heart 9 must occur. Given the assumption that the human heart 9 beats with a pulse of 80 beats per minute, the carrier 7 thus must execute a complete revolution at least 7½ times, preferably 12 through 15 times.

In the ideal case, the carrier 7 should rotate with a rotational speed n that is selected as high as possible. Under certain circumstances, however, it can be more beneficial to select the rotational speed n to be lower. This is particularly true when the motion of the heart 9 is strictly periodic. In this case, the rotational speed n of the carrier 7 is preferably selected such that the measured datasets of immediately successive rotational angles $\alpha$ are registered either during the phase range 16 of the same period or during the phase range 16 of the immediately following period.

Given as an example, the assumption of a constant (unchanging) cardiac frequency of 80/minute and a phase range 16 having a duration of 50 ms, a complete revolution of the carrier 7 therefore will be implemented in 700 ms.

The position of the phase range 16 can again be identified from an electrocardiogram 10 that is registered together with the image datasets. The position of the phase range 16 can be fundamentally arbitrary. The phase range 16 can, for example, lie in the resting phase 13 of the heart. It is of particular significance, however, when the phase range 16 lies in the beating phase 12 of the human heart 9.

For keeping the x-ray load on the patient 8 especially low, the x-ray source is preferably triggered with the electrocardiogram 10. This allows the patient 8 only to be transirradiated by the x-ray source 1 during the phase ranges 16. If the x-ray source 1 is not triggered, measured datasets are registered during all phases of the human heart 9. In this case, for example, the relevant phase ranges 16 can be subsequently determined in the image reconstruction.

FIG. 4 shows such a procedure schematically. Here, the reconstruction angle range $\beta$ is composed of phase angle ranges $\delta$, with the measured datasets of immediately successive rotational angles $\alpha$ being registered either during the phase range 16 thereof or during the phase range 16 of the immediately following period.

When the rotational speed n of the carrier 7 is not optimized in this way, the reconstruction angle range $\beta$, as schematically shown in FIG. 5, must be filled with phase angle ranges $\delta$ that are generally a purely stochastic permutation.

In order to be able to reconstruct an image of the heart 9 from the registered measured datasets, a measured dataset must be selected per rotational angle $\alpha$ from the registered measured datasets. Two selection methods are available for this purpose.

According to the first method, the measured datasets registered during the phase range 16 are combined for each phase range 16 to form a rotational angle group 17. A reference angle $\epsilon$ that corresponds with a phase reference point within the phase range 16 is determined for each rotational angle group 17. For example, the phase reference point can correspond to the middle or to the start of the phase range 16. For selecting the measured dataset that is then in fact used for the reconstruction of an image of the heart 9, the rotational angle group 17 is identified in each rotational angle $\alpha$ whose reference angle $\epsilon$ is maximally as large as that of the respective rotational angle $\alpha$. Within the rotational angle groups 17 identified in this way, the measured dataset of the rotational angle $\alpha$ of that rotational angle group 17 is then utilized wherein the difference between the respective rotational angle $\alpha$ and the respective reference angle $\epsilon$ is minimum.

An effective time resolution can be determined on the basis of the difference between the respective rotational angle $\alpha$ and the respective reference angle $\epsilon$ of the measured datasets utilized for the reconstruction of an image of the heart 9. The time resolution can be displayed together with the reconstructed image of the heart 9. The effective time resolution is the maximum of all differences between the respective rotational angle $\alpha$ and the respective reference angle $\epsilon$ of the measured datasets utilized for the reconstruction of an image of the heart 9.

Alternatively, the reconstruction angle range $\beta$ can be divided into a number of sub-angle ranges $\zeta$ of equal size, each having a respective sub-angle range reference angle $\xi$. The sub-angle range reference angle $\xi$ can, like the reference angle $\epsilon$, correspond to the middle or to the start of the sub-angle range $\zeta$. Per sub-angle range $\zeta$, the measured datasets of that rotational angle group 17 wherein the absolute value of the difference between the respective sub-angle range reference $\xi$ and the respective reference angle $\epsilon$ is minimum are then utilized for the reconstruction of an image of the heart 9.

In this method, the effective time resolution within which measured datasets are utilized for reconstruction of an image of the heart 9 is higher than the selected phase range, since the difference between the respective sub-angle range reference angle ζ and the respective reference angle ε is generally not equal to zero. The effective time resolution therefore is determined on the basis of the differences between the respective sub-angle range reference angle ξ and the respective reference angle ε of the measured datasets utilized for reconstruction of an image of the heart 9, the size of the sub-angle ranges ζ and the rotational speed n. The rotational speed n and the size of the sub-angle ranges ζ yield the minimum time resolution. This is then enlarged by the differences between the respective sub-angle range reference angle ξ and the respective reference angle ε of the measured datasets utilized for reconstruction of an image of the heart 9.

Figure 8:
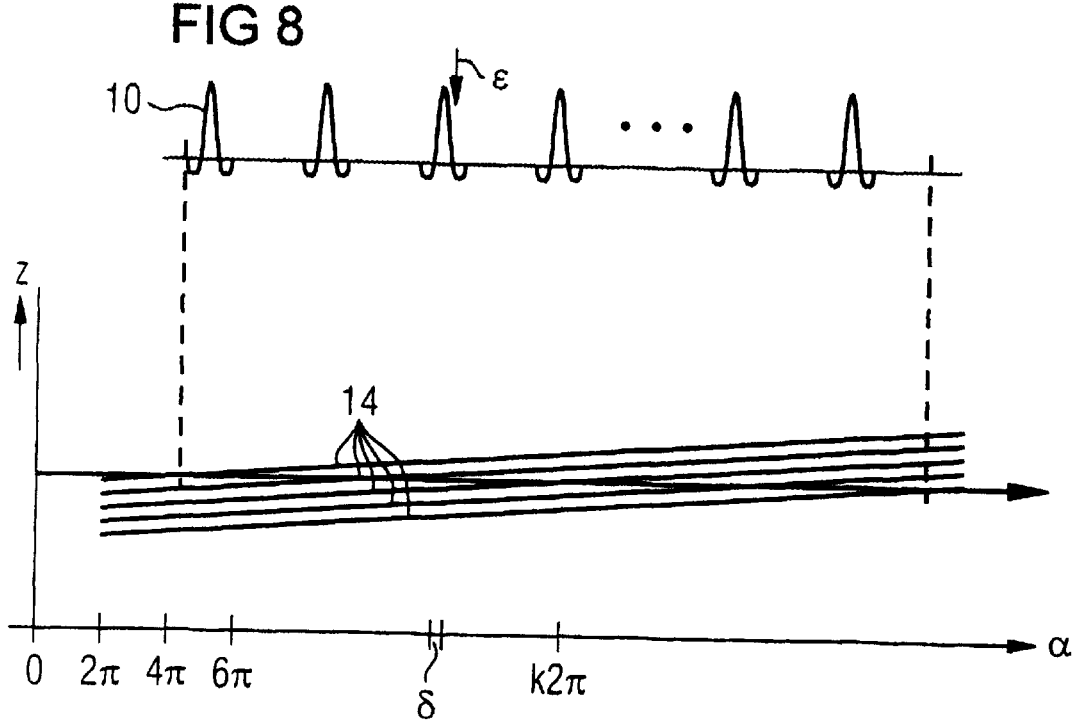
FIG. 8 schematically illustrates a further embodiment for the registration of measured datasets in accordance with the inventive method.

In both methods, a time discontinuity always occurs given a change from one rotational angle group 17 to another rotational angle group 17. The transition from one rotational angle group 17 to the next rotational angle group 17 therefore can be unsteady. This can lead to a diminished image quality in the reconstruction. The image quality, however, can be enhanced when the measured datasets given such a change are superimposed in a weighted manner in an overlap area. The overlap area covers at least the measured datasets allocated to mutually adjoining rotational angles α. For example, the last measured dataset of a rotational angle group 17 can be modified by weighting it ⅔ with its own value and ⅓ with the value of the first measured dataset of the following rotational angle group 17. Likewise, the first measured dataset of the following rotational angle group 17 can then be weighted ⅔ with its own value and ⅓ with the value of the last measured dataset from the preceding rotational angle group 17. This is schematically indicated in FIG. 8 with the broken lines. Even this slight modification already leads to a substantial improvement of the quality of the reconstructed image.

A time expansion also occurs due to the weighted superimposition of the measured datasets of the rotational angle groups 17. The size of the overlap area therefore is taken into consideration in the determination of the effective time resolution. This makes it possible for a skilled observer to estimate the quality of the reconstructed image.

In the implementation of a spiral scan, a relative displacement between the table 20 and thus the patient 8, and the carrier 7 with the measuring unit 1, 2, ensues in the direction of the rotational axis 6 with a feed rate v with continuous rotation of the carrier 7 with the measuring unit 1, 2.

When a feed rate v is selected such that the patient 8 (and, thus, of course, the heart 9 of the patient 8 as well) is displaced along the rotational axis 6 by a maximum of the detector width D during the sum of a motion phase and two reconstruction times T, it is possible to find an interconnected rotational angle range for each arbitrary displaced position z that lies in a resting phase of the heart 9. The reconstruction time T is thereby the time required for sweeping the reconstruction angle range β.

It is thus possible to find a value—for example, by linear interpolation—for arbitrary slice or displaced positions z from the measured data registered by neighboring detector line 3 through 5 that corresponds very well to the values that would have been registered with what is referred to as an axial scan at this displaced position z. An image of the object 9 then can be reconstructed with the totality of measured data required for the imaging using back-projection algorithms (for example, a convolution back-projection algorithm) that are well-known and employed in computed tomography.

This procedure is schematically shown in FIG. 7. The time t is entered toward the right in FIG. 7 and the displaced position z is entered toward the top. Further, an electrocardiogram 10 is entered in FIG. 7 whose peaks 11 identify the beating phases 12 of the heart 9. The resting phases 13 of the heart 9 lie therebetween. Further, obliquely proceeding lines 14 are entered in FIG. 7. These correspond to the displaced positions z of the individual detector lines 3 through 5. The length of the bar 15 corresponds to the time during which the carrier 7 rotates around the reconstruction angle range β.

As can be seen, a pair of lines 14 can be found for each displaced position z which lies in the same resting phase 13, sweeping an interconnected rotational angle γ thereat which is at least as large as the reconstruction angle range β, and in which, thus, a group of measured datasets which corresponds to an axial scan at this displaced position z can be constructed by linear interpolation.

Insofar as the resting phases 13 of the heart are long enough and the feed rate v is not too high, it is even possible to arbitrarily arrange the bar 15 within a resting phase 13 for each displaced position z. In this case, thus, it is even possible to portray the human heart 9 during different regions of its resting phases 13, for example shortly after beating or shortly before beating.

As already mentioned, the electrocardiogram 10 of the human heart 9 is monitored in order to be able to determine the resting phases 13 of the human heart 9 therefrom. As warranted, the electrocardiogram 10 also can be utilized in order to trigger the x-ray source 1 so that it emits x-rays only during the resting phases 13 of the heart 9. In this case, the x-ray stress on the patient 8 can be reduced. Moreover, the carrier 7 should rotate with the highest possible rotational speed n in this measured data registration method embodiment.

The above-described method cannot be applied when the human heart 9 is to be registered during a phase range 16 that lies in the beating phase 12. The phase range 16 has a time duration that is substantially shorter then the reconstruction time T. The phase range 16 can, for example, have a duration of 50 ms. During this time, the carrier 7 rotates only by 36°, even given a rotational speed n of 120 revolutions per minute, i.e. one-fifth of the minimum reconstruction angle range β. Nonetheless, the heart 9 also can be imaged in this phase range with the same computer tomograph. This occurs as follows.

As before, measured datasets allocated to each rotational angle α are respectively simultaneously registered by the detector lines 3 through 5 at a number of rotational angles α. The measured datasets are thereby registered at least during the phase range 16 of the periodic motion of the heart 9. The feed rate v, however, is now selected such that the object 9 experiences a number of periods during the feed by the detector width D. The number of periods is derived from the condition that the product of the number of periods and a phase angle range δ must at least correspond to the reconstruction angle range β. The phase angle range δ is thereby the angle swept by the carrier 7 during the duration of the phase range 16. As a safety margin, the plurality of periods should be 1½ through 2 times as great as the minimum number of periods.

The measured data registration method is schematically shown in FIG. 8. According to FIG. 8, the carrier 7 executes a number of rotations that typically lies between 10 and 20 until the patient 8 is displaced by the detector width D. During these rotations, the human heart 9 beats approximately 5 through 20 times. It is thus experiences 5 through 20 periods.

Let is be assumed as an example that the phase range 16 has a duration of 50 ms and that the carrier 7 rotates with a rotational speed n of 120 revolutions per minute. Given these assumptions, the carrier 7 sweeps a phase angle range δ=36° during a phase range 16. Given the further assumption that the reconstruction angle range β amounts to 180°, at least 5, preferably 8 through 10, beating phases 12 of the heart 9 would have to be covered. Given the assumption that the human heart 9 beats with a pulse of 80 beats per minute, the carrier 7 must thus implement a complete revolution at least 7½ times, preferably 12 through 15 times. During this number of revolutions, the patient 8 can be displaced no more than the detector width D.

In the ideal case, the carrier 7 should rotate with a rotational speed n that is selected as high as possible. Under certain circumstances, however, it can be more beneficial to select the rotational speed n to be lower. This is particularly true when the motion of the object 9 is strictly periodic. In this case, the rotational speed n of the carrier 7 is preferably selected such that the measured datasets of immediately following rotational angles α are registered either during the phase range 16 thereof or during the phase range 16 of the period immediately following thereupon.

Given the assumption of a constant cardiac frequency of 80 per minute and a phase range 16 having a duration of 50 ms, a complete revolution of the carrier 7 is therefore implemented, for example, preferably in 700 ms.

The position of the phase range 16 can again be identified from the electrocardiogram 10 that is registered together with the measured datasets. The position of the phase range 16 is thereby fundamentally arbitrary. The phase range 16 can, for example, lie in the resting phase 13 of the heart, however, it is of particular significance when the phase range 16 lies in the beating phase 12 of the human heart 9.

For keeping the x-ray load on the patient 8 especially low, the x-radiation source 1 is preferably triggered with the electrocardiogram 10. This allows the patient 8 only to be transirradiated during the phase ranges 16. When, on the other hand, the x-ray source 1 is not triggered, measured datasets are registered during all phases of the human heart 9. In this case, for example, the relevant phase ranges 16 can be subsequently determined during the image reconstruction.

FIG. 4 schematically shows such a procedure. Here, the reconstruction angle range β is composed of phase angle ranges δ, with the measured datasets of immediately following rotational angles α having registered either during the phase range 16 thereof or during the phase range 16 of the period following immediately thereupon.

If the rotational speed n of the carrier 7 is not optimized in this way, the reconstruction angle range β as schematically shown in FIG. 5, must be filled with phase angle ranges δ that are generally a purely stochastic permutation.

In order to be able to reconstruct an image of the object 9 from the registered measured datasets, one measured dataset must be selected per rotational angle α from the registered measured datasets. Two selection methods are available for this purpose.

According to the first method, the measured datasets registered during the phase range 16 are combined to form a respective rotational angle group 17 per phase range 16. A reference angle ε that corresponds with a phase reference point within the phase range 16 is determined for each rotational angle group 17. For example, the phase reference point can correspond to the middle or to the start of the phase range 16. For selecting the measured dataset that is then in face utilized for reconstruction of the object 9, the rotational angle groups 17 whose reference angle ε is maximally as large as the respective rotational angle α are then determined for each rotational angle α. Within the rotational angle groups 17 determined in this way, the measured dataset of the rotational angle α of that rotational angle group 17 wherein the difference between the respective rotational angle α and the respective reference angle ε is minimum is then utilized.

An effective time resolution can be determined on the basis of the differences between the respective rotational angle α and the respective reference angle ε of the measured datasets in fact utilized for reconstruction of the object 9. This time resolution can be displayed together with the reconstructed object 9. The effective time resolution is the maximum of all differences between the respective rotational angle α and the respective reference angle ε of the measured datasets utilized for reconstruction of the object 9.

Alternatively, the reconstruction angle range β can be divided into a number of sub-angle ranges ζ of equal size each having a sub-angle range reference angle ξ. The sub-angle range reference angle ξ, like the reference angle ε, can correspond to the middle or to the start of the sub-angle range ζ. The measured datasets of that rotational angle group 17 wherein the absolute value of the difference between the respective sub-angle range reference angle ξ and the respective reference angle ε is minimum are then utilized per sub-angle range ζ for reconstruction of the object 9.

In this method embodiment, the effective time resolution within which measured datasets are utilized for reconstruction of the object 9 is greater then the selected phase range. The difference between the respective sub-angle range reference angle ξ, namely, and the respective reference angle ε is generally not zero. The effective time resolution is therefore determined on the basis of the differences between the respective sub-angle range reference angle ξ and the respective reference angle ε of the measured datasets in fact utilized for reconstruction of the object 9, the size of the sub-angle range ζ and the rotational speed n. The rotational speed n and the size of the sub-angle ranges ζ yield the minimum time resolution. This is then enlarged by the differences between the respective sub-angle range reference angle ξ and the respective reference angle ε of the measured datasets in fact utilized for reconstruction of the object 9.

Figure 6:
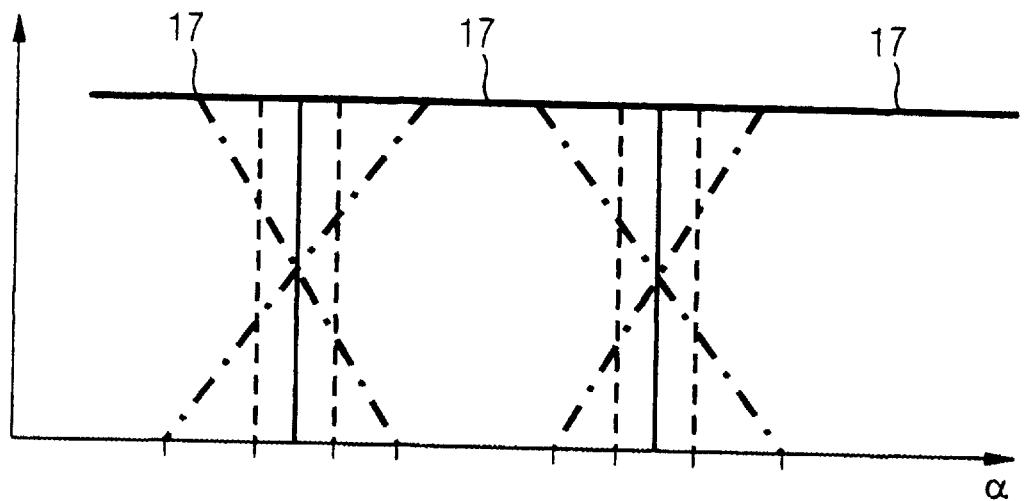
FIG. 6 schematically illustrates a weighting curve used in the inventive method.

In both method embodiments, a time discontinuity also always occurs given a change from one rotational angle group 17 to another rotational angle group 17. The transition from one rotational angle group 17 to the next rotational angle group 17 can therefore be unsteady. This can lead to a diminished image quality in the reconstruction. The image quality, however, can be enhanced when the measured datasets given such a change are superimposed in a weighted manner in an overlap area. The overlap area covers at least the measured datasets allocated to mutually adjoining rotational angles α. For example, the last measured dataset of a rotational angle group 17 can be modified by weighting it ⅔ with its own value and ⅓ with the value of the first measured dataset of the following rotational angle group 17. Likewise, the first measured dataset of the following rotational angle group 17 can then be weighted ⅔ with its own value and ⅓ with the value of the last measured dataset of the preceding rotational angle group 17. This is schematically indicated in FIG. 6 by the broken lines. Even this slight modification already leads to a substantial improvement of the quality of the reconstructed image.

A time expansion also occurs due to the weighted superimposition of the measured datasets of the rotational angle groups 17. The size of the overlap area therefore is taken into consideration in the determination of the effective time resolution. This makes it possible for a trained observer to estimate the quality of the reconstructed image.

The inventive image reconstruction method, in particular, makes it possible to generate qualitatively high-grade measured datasets within a breath-holding pause of the patient 8 with which the entire heart 9 can be portrayed.

Although modifications and changes may be suggested by those skilled in the art, it is the intention of the inventors to embody within the patent warranted hereon all changes and modifications as reasonably and properly come within the scope of their contribution to the art.

We claim as our invention:

1. An image reconstruction method for obtaining an image of a periodically moving object, experiencing successive periods each having a motion phase and a resting phase, using a detector unit having a first detector line and a last detector line disposed on a carrier opposite an x-ray source, said carrier being rotatable around a rotational axis and said detector lines being oriented substantially at a right angle relative to said rotational axis, said method comprising the steps of:

rotating said carrier at a rotational speed around said rotational axis so that said x-ray source proceeds through rotational angles;

for each rotational angle in a plurality of rotational angles, simultaneously registering respective measured datasets from the respective detector lines during a plurality of said periods;

selecting a phase reference point in each of said periods and identifying a phase range in each of said periods relative to said phase reference point, and registering said measured datasets at least during the respective phase ranges of said periods;

identifying a duration of said phase ranges and identifying a phase angle range which is swept during each phase range, and selecting said plurality of periods so that a product of said plurality of periods and said phase angle range corresponds to a reconstruction angle range required for reconstruction of an image of said object; and reconstructing said image of said object from said measured datasets using a three-dimensional back-projection algorithm, comprising for each phase range, combining the measured datasets registered during that phase range to form a rotational angle group;

for each rotational angle group, determining a reference angle corresponding to the phase reference point for that phase range during which the said measured datasets are combined;

for each rotational angle, identifying each rotational angle group having a reference angle which is at least as large as that rotational angle, to obtain a set of rotational angle groups; and identifying measured datasets, as identified measured datasets, of a rotational angle group within said set of rotational angle groups for which a difference between the rotational angle and the reference angle is minimum, and utilizing only said identified measured datasets for reconstructing said image.

2. An image reconstruction method as claimed in claim 1 comprising obtaining said measured datasets from a human heart as said object, and wherein said phase range lies within a beating phase of said human heart.

3. An image reconstruction method as claimed in claim 2 comprising obtaining an electrocardiogram of said human heart for determining said phase range.

4. An image reconstruction method as claimed in claim 2 comprising triggering said x-ray source using said electrocardiogram so that said human heart is irradiated with x-rays only during said phase ranges.

5. An image reconstruction method as claimed in claim 1 comprising selecting said rotational speed of said carrier so that respective measured datasets of successive rotational angles are registered during a phase range in a single one of said periods or during a phase range of a period immediately following said one of said periods.

6. An image reconstruction method as claimed in claim 1 comprising selecting said rotational speed of said carrier as high as possible.

7. An image reconstruction method as claimed in claim 1 comprising identifying a time resolution dependent on said difference between the rotational angle and the reference angle of the rotational angle group for the identified measured datasets, and displaying said time resolution together with said image.

8. An image reconstruction method as claimed in claim 1 wherein a change from one rotational angle group to another rotational angle group proceeds through an overlap area, and comprising the step of superimposing measured datasets in said overlap area with respective weightings from said one rotational angle group and said another rotational angle group.

9. An image reconstruction method as claimed in claim 8 comprising identifying a time resolution dependent on said difference between the rotational angle and the reference angle of the rotational angle group for the identified measured datasets, and displaying said time resolution together with said image, and determining a size of said overlap area dependent on said time resolution.

10. An image reconstruction method for obtaining an image of a periodically moving object, experiencing successive periods each having a motion phase and a resting phase, using a detector unit having a first detector line and a last detector line disposed on a carrier opposite an x-ray source, said carrier being rotatable around a rotational axis and said detector lines being oriented substantially at a right angle relative to said rotational axis, said method comprising the steps of:

rotating said carrier at a rotational speed around said rotational axis so that said x-ray source proceeds through rotational angles;

for each rotational angle in a plurality of rotational angles, simultaneously registering respective measured datasets from the respective detector lines during a plurality of said periods;

selecting a phase reference point in each of said periods and identifying a phase range in each of said periods relative to said phase reference point, and registering said measured datasets at least during the respective phase ranges of said periods;

identifying a duration of said phase ranges and identifying a phase angle range which is swept during each phase range, and selecting said plurality of periods so that a product of said plurality of periods and said phase angle range corresponds to a reconstruction angle range required for reconstruction of an image of said object; and reconstructing said image of said object from said measured datasets using a three-dimensional back-projection algorithm, comprising dividing said reconstruction angle range into a plurality of sub-angle ranges of equal size, each having a sub-angle range reference angle;

for each phase range, combining the measured datasets to form a rotational angle group;

identifying a reference angle corresponding to the phase reference point for that phase range for which the measured datasets are combined; and identifying measured datasets, as identified measured datasets, of a rotational group for which an absolute value of a difference between the sub-angle range reference angle and the reference angle is minimum, and utilizing only said identified measured datasets in each sub-angle range for reconstructing said image.

11. An image reconstruction method as claimed in claim 10 comprising identifying a time resolution dependent on said difference between said sub-angle range reference angle and said reference angle of said identified measured datasets, and displaying said time resolution together with said image.

12. An image reconstruction method as claimed in claim 10 wherein a change from one rotational angle group to another rotational angle group proceeds through an overlap area, and comprising the step of superimposing measured datasets in said overlap area with respective weightings from said one rotational angle group and said another rotational angle group.

13. An image reconstruction method as claimed in claim 12 comprising identifying a time resolution dependent on said difference between said sub-angle range reference angle and said reference angle of said identified measured datasets, and displaying said time resolution together with said image, and determining a size of said overlap area dependent on said time resolution.

14. An image reconstruction method for obtaining an image of a periodically moving object, experiencing successive periods each having a motion phase and a resting phase, using a detector unit having a first detector line and a last detector line disposed on a carrier opposite an x-ray source, said carrier being rotatable around a rotational axis and said detector lines being oriented substantially at a right angle relative to said rotational axis and being spaced from each other parallel to said rotational axis by a detector width, said method comprising the steps of:

rotating said carrier at a rotational speed around said rotational axis so that said x-ray source proceeds through rotational angles;

for each rotational angle, simultaneously registering respective measured datasets allocated to the respective rotational angle during which said measured datasets were registered;

in each of said periods, identifying phase ranges having respective phase reference points, and registering the respective measured datasets at least during said respective phase ranges;

selecting said feed rate so that said object experiences a plurality of periods during displacement by said detector width;

identifying a duration of the respective phase ranges;

selecting said phase range so that a product of said plurality of periods and a phase angle range swept during said phase range is at least equal to a reconstruction angle range required for reconstruction of said image; and reconstructing said image of said object from said measured datasets using a three-dimensional back-projection algorithm, comprising for each phase range, combining the measured datasets registered during that phase range to form a rotational angle group;

for each rotational angle group, determining a reference angle corresponding to the phase reference point for that phase range during which the said measured datasets are combined;

for each rotational angle, identifying each rotational angle group having a reference angle which is at least as large as that rotational angle, to obtain a set of rotational angle groups; and identifying measured datasets, as identified measured datasets, of a rotational angle group within said set of rotational angle groups for which a difference between the rotational angle and the reference angle is minimum, and utilizing only said identified measured datasets for reconstructing said image.

15. An image reconstruction method as claimed in claim 14 comprising obtaining said measured datasets from a human heart as said object, and wherein said phase range lies within a beating phase of said human heart.

16. An image reconstruction method as claimed in claim 15 comprising obtaining an electrocardiogram of said human heart for determining said phase range.

17. An image reconstruction method as claimed in claim 16 comprising triggering said x-ray source using said electrocardiogram so that said human heart is irradiated with x-rays only during said phase ranges.

18. An image reconstruction method as claimed in claim 14 comprising selecting said rotational speed of said carrier so that respective measured datasets of successive rotational angles are registered during a phase range in a single one of said periods or during a phase range of a period immediately following said one of said periods.

19. An image reconstruction method as claimed in claim 14 comprising selecting said rotational speed of said carrier as high as possible.

20. An image reconstruction method as claimed in claim 14 comprising identifying a time resolution dependent on said difference between the rotational angle and the reference angle of the rotational angle group for the identified measured datasets, and displaying said time resolution together with said image.

21. An image reconstruction method as claimed in claim 14 wherein a change from one rotational angle group to another rotational angle group proceeds through an overlap area, and comprising the step of superimposing measured datasets in said overlap area with respective weightings from said one rotational angle group and said another rotational angle group.

22. An image reconstruction method as claimed in claim 21 comprising identifying a time resolution dependent on said difference between the rotational angle and the reference angle of the rotational angle group for the identified measured datasets, and displaying said time resolution together with said image, and determining a size of said overlap area dependent on said time resolution.

23. An image reconstruction method for obtaining an image of a periodically moving object, experiencing successive periods each having a motion phase and a resting phase, using a detector unit having a first detector line and a last detector line disposed on a carrier opposite an x-ray source, said carrier being rotatable around a rotational axis and said detector lines being oriented substantially at a right angle relative to said rotational axis and being spaced from each other parallel to said rotational axis by a detector width, said method comprising the steps of:

rotating said carrier at a rotational speed around said rotational axis so that said x-ray source proceeds through rotational angles;

for each rotational angle, simultaneously registering respective measured datasets allocated to the respective rotational angle during which said measured datasets were registered;

in each of said periods, identifying phase ranges having respective phase reference points, and registering the respective measured datasets at least during said respective phase ranges;

selecting said feed rate so that said object experiences a plurality of periods during displacement by said detector width;

identifying a duration of the respective phase ranges;

selecting said phase range so that a product of said plurality of periods and a phase angle range swept during said phase range is at least equal to a reconstruction angle range required for reconstruction of said image; and reconstructing said image of said object from said measured datasets using a three-dimensional back-projection algorithm, comprising dividing said reconstruction angle range into a plurality of sub-angle ranges of equal size, each having a sub-angle range reference angle;

for each phase range, combining the measured datasets to form a rotational angle group;

identifying a reference angle corresponding to the phase reference point for that phase range for which the measured datasets are combined; and identifying measured datasets, as identified measured datasets, of a rotational group for which an absolute value of a difference between the sub-angle range reference angle and the reference angle is minimum, and utilizing only said identified measured datasets in each sub-angle range for reconstructing said image.

24. An image reconstruction method as claimed in claim 23 comprising identifying a time resolution dependent on said difference between said sub-angle range reference angle and said reference angle of said identified measured datasets, and displaying said time resolution together with said image.

25. An image reconstruction method as claimed in claim 23 wherein a change from one rotational angle group to another rotational angle group proceeds through an overlap area, and comprising the step of superimposing measured datasets in said overlap area with respective weightings from said one rotational angle group and said another rotational angle group.

26. An image reconstruction method as claimed in claim 25 comprising identifying a time resolution dependent on said difference between said sub-angle range reference angle and said reference angle of said identified measured datasets, and displaying said time resolution together with said image, and determining a size of said overlap area dependent on said time resolution.

* * * * *